United States Patent
Adriani

(10) Patent No.: US 8,973,448 B2
(45) Date of Patent: Mar. 10, 2015

(54) DEVICE FOR SAMPLING WORKING LIQUIDS OF INDUSTRIAL MACHINES

(76) Inventor: Giuseppe Adriani, Florence (IT)

( * ) Notice: Subject to any disclaimer, the term of this patent is extended or adjusted under 35 U.S.C. 154(b) by 426 days.

(21) Appl. No.: 13/382,253

(22) PCT Filed: Jul. 17, 2009

(86) PCT No.: PCT/IT2009/000317
§ 371 (c)(1),
(2), (4) Date: Jan. 4, 2012

(87) PCT Pub. No.: WO2011/007377
PCT Pub. Date: Jan. 20, 2011

(65) Prior Publication Data
US 2012/0096959 A1   Apr. 26, 2012

(51) Int. Cl.
*G01N 1/14* (2006.01)
*G01N 1/20* (2006.01)

(52) U.S. Cl.
CPC .......... *G01N 1/14* (2013.01); *G01N 2001/1418* (2013.01); *G01N 2001/2078* (2013.01)
USPC ..................................... 73/864.73

(58) Field of Classification Search
None
See application file for complete search history.

(56) References Cited

U.S. PATENT DOCUMENTS

| | | | | |
|---|---|---|---|---|
| 3,357,601 | A * | 12/1967 | Crawford et al. | 222/397 |
| 3,618,393 | A * | 11/1971 | Principe et al. | 73/864.52 |
| 3,833,000 | A * | 9/1974 | Bridgman | 604/118 |
| 3,856,901 | A * | 12/1974 | Neumann et al. | 261/18.2 |
| 4,378,026 | A | 3/1983 | Bauer | |
| 4,548,088 | A | 10/1985 | Hood, Jr. | |
| 4,925,627 | A | 5/1990 | Johnson | |
| 4,930,360 | A | 6/1990 | Tan | |
| 5,372,143 | A * | 12/1994 | Bernes et al. | 600/575 |
| 5,463,909 | A * | 11/1995 | Eldridge | 73/864.52 |
| 5,621,180 | A * | 4/1997 | Simon et al. | 73/864.52 |
| 5,976,468 | A * | 11/1999 | Godec et al. | 422/501 |
| 6,112,759 | A | 9/2000 | Hsu | |
| 6,363,801 | B1 * | 4/2002 | Carnahan | 73/864.11 |
| 6,883,535 | B1 | 4/2005 | Cromwell et al. | |
| 2001/0035208 | A1 | 11/2001 | Cromwell et al. | |
| 2003/0164051 | A1* | 9/2003 | Kunimune et al. | 73/863.23 |
| 2008/0227210 | A1* | 9/2008 | Smith | 436/86 |
| 2009/0100902 | A1 | 4/2009 | Miller et al. | |

FOREIGN PATENT DOCUMENTS

| | | |
|---|---|---|
| DE | 101 05 510 A1 | 8/2002 |
| EP | 1 236 997 A2 | 9/2002 |
| WO | 96/04540 A1 | 2/1996 |

* cited by examiner

*Primary Examiner* — Robert R Raevis
(74) *Attorney, Agent, or Firm* — Lucas & Mercanti, LLP

(57) ABSTRACT

A device for sampling working liquids of industrial machines, comprising a container (2) having an aperture (3) and a closing member (4) engaged to said aperture (3) for fluid-tight sealing same aperture. The pressure inside said container (2) is below 101000 Pa.

5 Claims, 3 Drawing Sheets

DEVICE FOR SAMPLING WORKING LIQUIDS OF INDUSTRIAL MACHINES

CROSS-REFERENCE TO RELATED APPLICATION

This application is a 371 of PCT/IT2009/000317, filed Jul. 17, 2009, the contents of which are incorporated herein by reference.

TECHNICAL FIELD OF THE INVENTION

The present invention refers to a device for sampling working liquids of industrial machines".

In the field of industrial machinery operation, and especially of the machines service, there is a growing spread of so-called "preventive maintenance". Such type of maintenance provides for foretelling, that is, anticipating and thus avoiding, a failure or a malfunction of a machine by analysing the operating parameters thereof.

In particular, it is possible to diagnose the state of operation of a machine by analysing the working fluids or liquids thereof.

In fact, the chemical-physical analysis of a machine's working liquids (e.g., the lubricating oil) makes it possible to establish whether malfunctions or abnormal wear are, taking place inside the machine.

If, for example, ferrous materials were to be found inside the lubricating oil of a machine, it would mean that some mechanical part of the machine is wearing out abnormally.

Again, the presence of refrigerating liquid inside the lubricating oil would be an index of the fact that some sealing element is no longer able to carry out its design function.

In order to analyse the working liquid of the machine is obviously necessary to take the liquid directly out of the machine's case or tank.

STATE OF ART

To this purpose, devices for sampling working liquids of industrial machines are known which comprise a container located below tapping points (usually provided with shutoff valves) formed in the machine.

The operating fluid exits, due to gravity or the operating pressure, from the tapping point and is collected into the container. The container is then closed and delivered to a laboratory for analysis.

In case the working liquid has to be drawn from machines that do not exhibit tapping points under pressure, sampling devices are known consisting of suitable syringes which aspirate the working liquid from the machine.

The use of such syringes, however, results difficult, especially in cases in which the working liquid is particularly viscous.

In any case, both the tapping devices above described exhibit a major drawback.

Such drawback is related to the possible contamination when tapping the sampled working liquid.

It is stressed that even the contamination due to the atmospherical dust may alter significantly the result of a test performed on the working liquid being sampled.

In fact, the amount of liquid being withdrawn is generally in the order of 100 cm$^3$.

The significant quantities of foreign material entrained by the working liquid and determining the machine's operation diagnosis, that is, the grams of substances (metals, powders, water) per cubic meter of working liquid, are measured in concentrations of few parts per million.

It is then evident that even a grain of sand of 0.5 g (per 100 cm$^3$ of working liquid being tapped) could lead to think to a state of contamination of several hundreds of grams of sand in the machine's circuit, with a clear error in the diagnosis of the machine's operation.

In this context, the technical task of the present invention is to propose an apparatus for making a device for sampling working liquids of industrial machines which overcomes the above cited drawbacks.

BRIEF SUMMARY OF THE INVENTION

In particular, it is an object of the present invention to provide a device for sampling working liquids of industrial machines which prevents any accidental contamination of the working liquid being sampled.

A further object of the invention is to provide a device for sampling working liquids of industrial machines which is of easy and rapid use.

These and further objects are substantially achieved by a device for sampling liquids of industrial machines as disclosed in one or more appended claims. Further characteristics and advantages of the present invention will appear more clearly by a reading of a preferred but non-exclusive embodiment of a device for sampling working liquids of industrial machines, according to the invention.

DETAILED DESCRIPTION OF THE DRAWINGS

Such description is given with reference to the attached figure, the later also having a purely exemplary and thus non-limiting purpose, wherein.

DETAILED DESCRIPTION OF THE INVENTION

Figure 1:
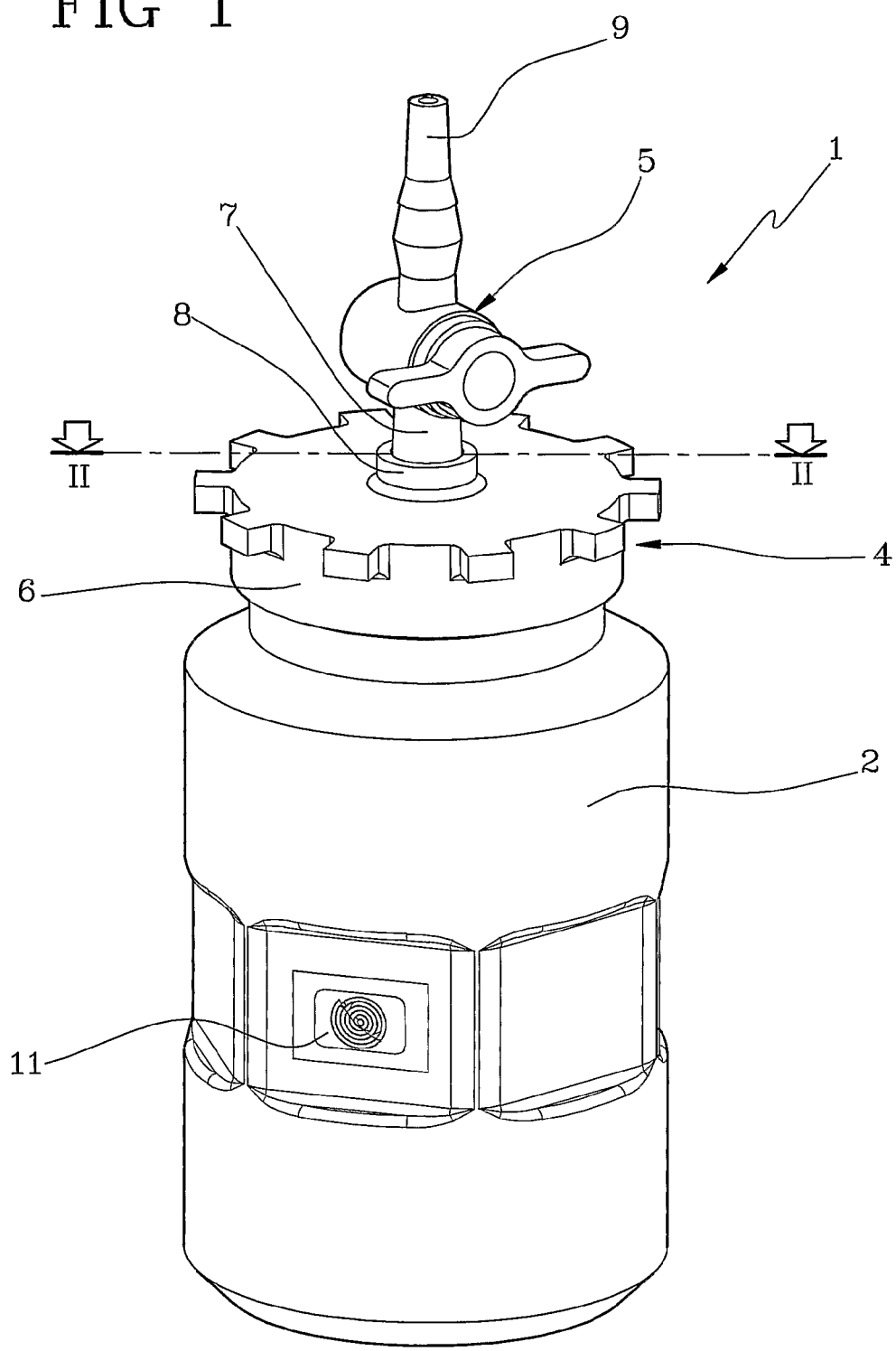
FIG. 1 is a perspective view of a device for sampling liquids of industrial machines according to the present invention, with some parts taken away for a better illustration of others.

With reference to the attached figures, numeral 1 indicates in the whole a device for sampling liquids of industrial machines, according to the present invention.

With the wording "working liquids of industrial machines" it is to be meant, in the context of the present invention, those liquids necessary for the operation of machines, for example lubricating oil, refrigerating liquid.

The industrial machines may be of any type, including vehicles for motor transport.

The device 1 comprises a container 2 having an aperture 3 and a closing member 4 engaged with the aperture 3.

The closing member 4 has the function of fluid-tight sealing the container 2, that is, of inhibiting the transfer of fluid between the external environment and the inside of the container 2.

Advantageously, the pressure inside the container 2, sealed by the closing member 4, is less than the atmospheric pressure, that is, is less than 101000 Pa.

In particular, the pressure inside the container 2 is between 6000 Pa and 60000 Pa.

Preferably, the pressure inside the container 2 is between 8000 Pa and 50000 Pa.

In particular, the pressure inside the container 2 is about 8000 Pa the moment the device 1 is produced and increases slowly over the time until it reaches about 50000 at the end of the period of possible use thereof (which is in the order of few months since the date of production).

In this view, the container 2 is made from high density PVC.

The pressure values above indicated refer to the device 1 before the same is used, as will appear clearly later on from the present description.

The device 1 also comprises a shutoff element 5 that can be switched between a closing position, in which the container 2 is fluid-tight sealed, and an opening position in which the container 2 is put into fluid communication with the external environment.

The shutoff element 5 is operatively associated with the closing member 4.

Preferably, the closing member comprises a screw plug 6 engaged to the aperture 3 of container 2.

Figure 2:
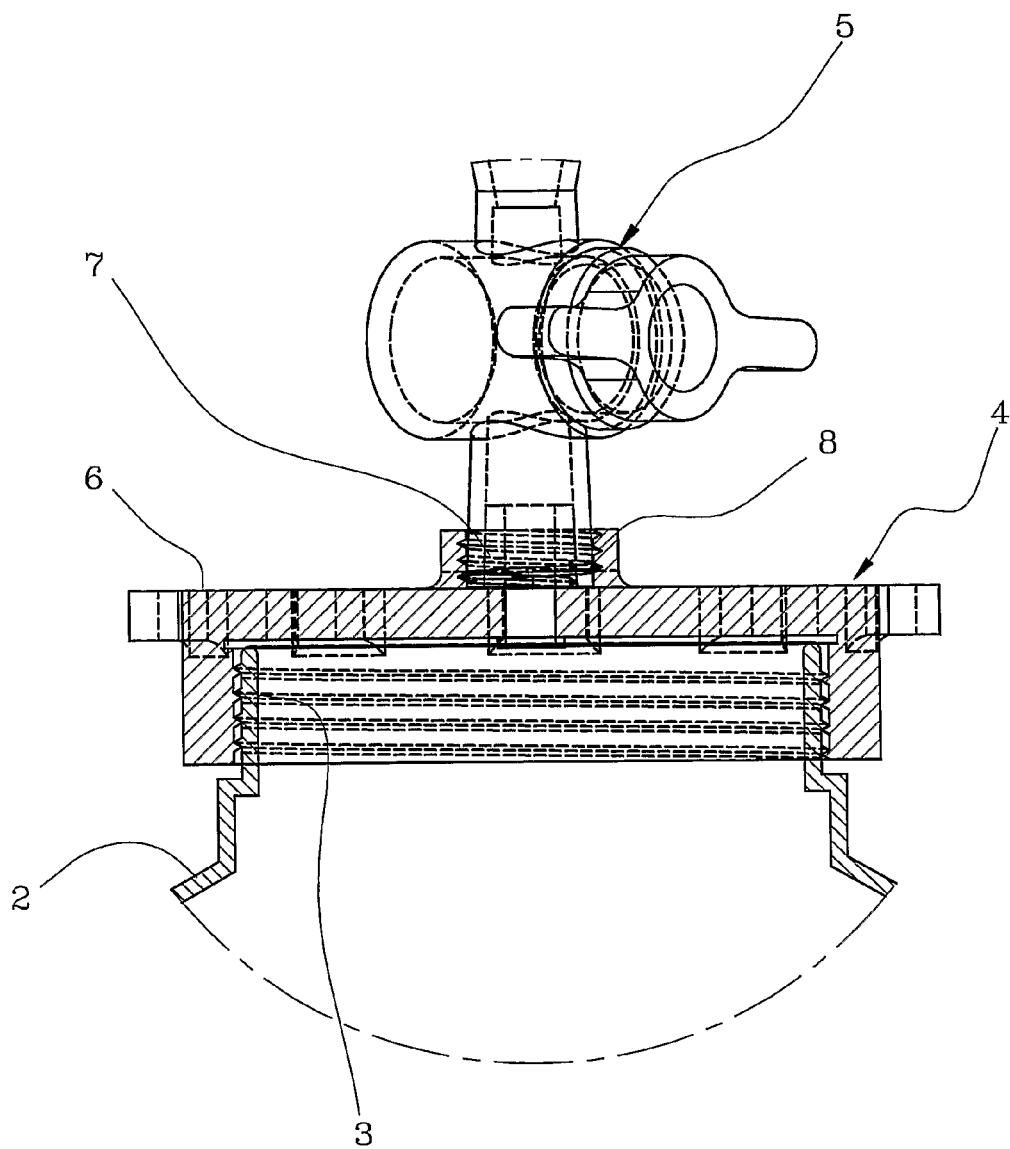
FIG. 2 is a section taken on line II-II of a portion of the device shown in FIG. 1.

In the preferred embodiment of the invention, the screw plug 6 encircles and embraces the peripheral edge of the aperture 3 and exhibits a thread pitch of 1 millimeter (see FIG. 2).

As illustrated in the attached figures, the shutoff element 5 is engaged to the screw plug 6 on the side opposite to the aperture of container 2.

Preferably, the shutoff member 5, is a cock provided with a valve able to either allow or inhibit the passage of fluid between the container 2 and the external environment.

In particular, the cock 5 comprises a first threaded end 7 (FIG. 2) screwed in a threaded hole 8 of the screw plug 6 to provide a tight-fluid seal.

The opposite end of the first end 7 of cock 5 is provided with a spout 9 intended to receive for engagement a conduit connectable to the machine and from which the liquid to be sampled is to be taken out.

Figure 3:
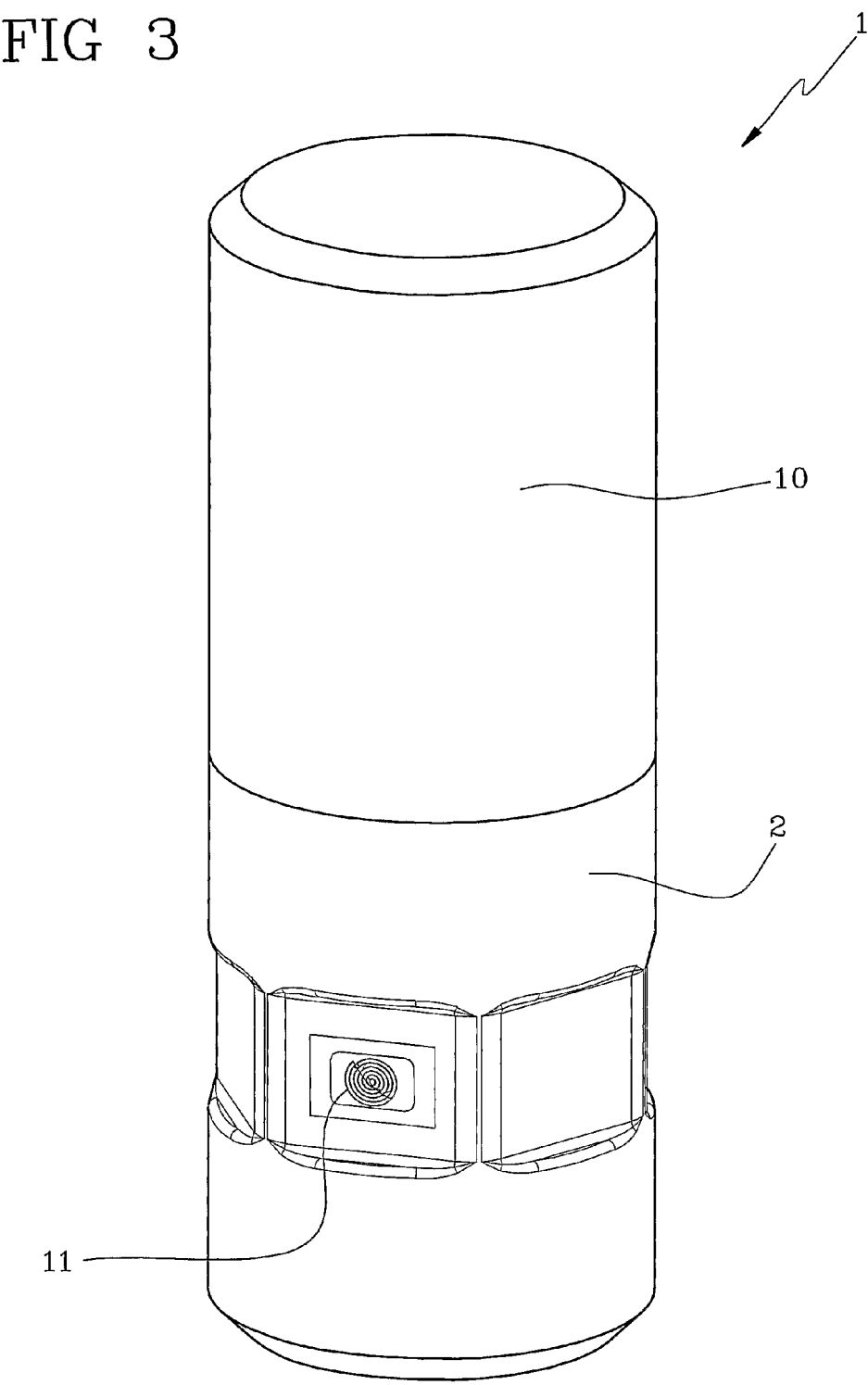
FIG. 3 is a perspective view of the device shown in FIG. 1 in its whole.

The device 1 also comprises a lid 10 removably engageable onto the container 2 (FIG. 3). The lid 10 covers completely both the screw plug 6 and the shutoff element 5, so as to make both the shutoff element 5 and the screw plug 6 fully inaccessible.

In the preferred embodiment of the invention, the device comprises an RFID (Radio Frequency IDentification) tag 11 holding information related to the container 2.

With the wording "information related to the container" it is intended, in the context of the present invention, one or more of the following: date of production of the container, initial pressure inside the container, expiry of device's utilization, and the like.

The RFID tag 11 is firmly associated with the container 2, in particular on an outer wall thereof.

The RFID tag 11 allows a safe and efficient traceability of the device 1, thereby improving stock management, supply orders, and disposal of devices 1 no longer used.

The device 1 is used as described herebelow.

The device 1 is connected to the machine from which the working liquid is to be withdrawn for subsequent laboratory analysis.

The shutoff element 5 is kept in the closing position so as to have the device 1 and the machine physically connected, but to maintain as well an interruption of fluid transfer. It should be appreciated that, in this configuration, the system device-machine is fluid-isolated from the external environment.

The shutoff element 5 is then shifted into the opening position so as to establish a fluid-connection between the machine and the inside of container 2.

In this configuration, the vacuum created inside the container 2 upon the production of device 1, draws liquid from the machine to the same container 2.

The container 2 begins then to fill up with the machine's working liquid.

It is pointed out that in this stage, the system device-machine is maintained isolated from the outside.

When the amount of working liquid inside the container 2 reaches a preset quantity (sufficient to carry out the laboratory analysis), the shutoff element 5 is shifted into the closing position, thereby cutting off again the communication between the machine and the device.

The device is then disconnected from the machinery and the lid 10 is applied, so that both the screw plug 6 and shutoff element 5 are not accessible (and the container 2, therefore, cannot be opened, neither accidentally).

The device is then delivered to the laboratory for carrying out the necessary analysis on the working liquid taken out from the machine.

It is to be noted that throughout the above described process, there is no possibility for the withdrawn working liquid to be contaminated from the environment outside the machine.

The invention achieves the proposed objects.

The fact that the container 2 is provided with a closing member that isolates it from the outside, and that the pressure inside the same container is below 101000 Pa, in particular ranging from 6000 to 60000 Pa, makes it possible to withdraw working liquid from the machine by avoiding any contamination of the liquid, as clearly appearing from the description of the operation of device 1.

Moreover, the device 1 is of easy and rapid use, as clearly appearing from the description of the operation thereof.

The invention claimed is:

1. Device for sampling working liquids of industrial machines, comprising a container having an aperture and a closing member engaged to said aperture for fluid-tight sealing same aperture;
   wherein the pressure inside said container is sufficient to withdraw a working liquid from a machine and ranges from about 6000 Pa to about 60000 Pa;
   wherein said closing member includes a shutoff element switchable between a closing position in which said container is fluid-tight sealed and an opening position in which said container is in fluid-communication with the outside environment;
   wherein said closing member includes a screw plug engaged to said aperture of said container, said screw plug having a flat top surface, said shutoff element being adapted to said screw plug and includes a first threaded end screwed in a threaded hole of said flat top surface of the screw plug to provide a fluid-tight seal; and
   a lid removably engageable onto said container; said lid covering said screw plug and said shutoff element so as to make said screw plug and said shutoff element fully inaccessible.

2. Device according to claim 1, wherein the pressure inside said container is between 8000 and 50000 Pa.

3. Device according to claim 1, comprising a spout intended to receive for engagement a conduit connectable to the machine; said spout being in fluid communication with said shutoff element on a side opposite to said aperture of container.

4. Device according to claim 1 wherein said container is made of PVC.

5. Device according to claim 1, further comprising an RFID tag holding information related to the container.

\* \* \* \* \*